(12) United States Patent
Cage et al.

(10) Patent No.: US 8,473,034 B2
(45) Date of Patent: Jun. 25, 2013

(54) SYSTEM AND METHOD FOR FEEDING TUBE PLACEMENT

(75) Inventors: Logan Michael Cage, Bloomington, IN (US); Peter William Sargent, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 152 days.

(21) Appl. No.: 13/040,653

(22) Filed: Mar. 4, 2011

(65) Prior Publication Data

US 2012/0226144 A1 Sep. 6, 2012

(51) Int. Cl.
*A61B 8/12* (2006.01)
*A61M 25/095* (2006.01)

(52) U.S. Cl.
USPC .......................... 600/424; 604/910; 604/516

(58) Field of Classification Search
USPC .................... 604/910, 516; 600/433, 424
See application file for complete search history.

(56) References Cited

U.S. PATENT DOCUMENTS

| | | | |
|---|---|---|---|
| 5,037,387 A | 8/1991 | Quinn et al. | 604/51 |
| 5,201,314 A * | 4/1993 | Bosley et al. | 600/458 |
| 5,314,409 A | 5/1994 | Sarosiek et al. | 604/101 |
| 5,318,530 A | 6/1994 | Nelson, Jr. | 604/96 |
| 5,871,467 A | 2/1999 | Reuning et al. | 604/96 |
| 6,322,495 B1 | 11/2001 | Snow et al. | 600/114 |
| 6,589,213 B2 | 7/2003 | Reydel | 604/175 |
| 6,767,339 B2 | 7/2004 | Reydel | 604/175 |
| 6,960,199 B2 | 11/2005 | Burkett et al. | 604/514 |
| 7,509,174 B2 * | 3/2009 | Imran et al. | 604/516 |
| 2005/0096634 A1 * | 5/2005 | Madsen | 604/516 |
| 2006/0259115 A1 * | 11/2006 | Case et al. | 623/1.11 |
| 2008/0147048 A1 * | 6/2008 | Deutsch | 604/541 |
| 2008/0228066 A1 | 9/2008 | Waitzman | 600/424 |
| 2010/0097373 A1 * | 4/2010 | Besz et al. | 600/424 |

FOREIGN PATENT DOCUMENTS

| | | |
|---|---|---|
| EP | 1642612 A2 | 4/2006 |
| EP | 1834661 A1 | 9/2007 |
| WO | WO 2005/097042 A1 | 10/2005 |

OTHER PUBLICATIONS

Hernandez-Socorro et al. "Bedside sonographic-guided versus blind nasoenteric feeding tube placement in critically ill patients." Critical Care Medicine. vol. 24(10), Oct. 1996, pp. 1690-1694.*
Shung. "Diagnostic Ultrasound Imaging and Blood Flow Measurements." 2006. Taylor & Francis Group, LLC. Chapter 2.6, pp. 17-20.*

* cited by examiner

*Primary Examiner* — Long V. Le
*Assistant Examiner* — Colin T Sakamoto
(74) *Attorney, Agent, or Firm* — Brinks Hofer Gilson & Lione

(57) ABSTRACT

A system and method for monitoring the placement of a feeding tube in the jejunum of a patient includes a system comprising a feeding tube and a tubular member received in a passageway extending through the feeding tube. The tubular member is sized relative to the feeding tube such that an echogenic distal length of the tubular member extends distal to the open distal end of the feeding tube. The distal end of the assembly is advanced into the small intestine of the patient, and a negative pressure is drawn through an opening in the distal length of the tubular member to draw the tubular member distal length into juxtaposition with a wall of the small intestine. The position of the assembly in the small intestine may be observed in real time via ultrasound visualization of the echogenic portion.

18 Claims, 3 Drawing Sheets

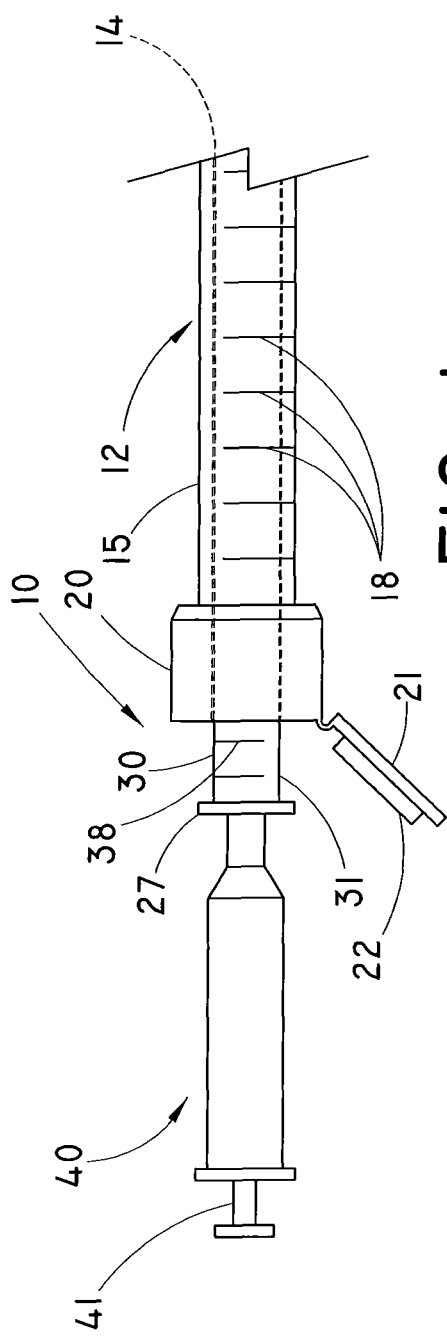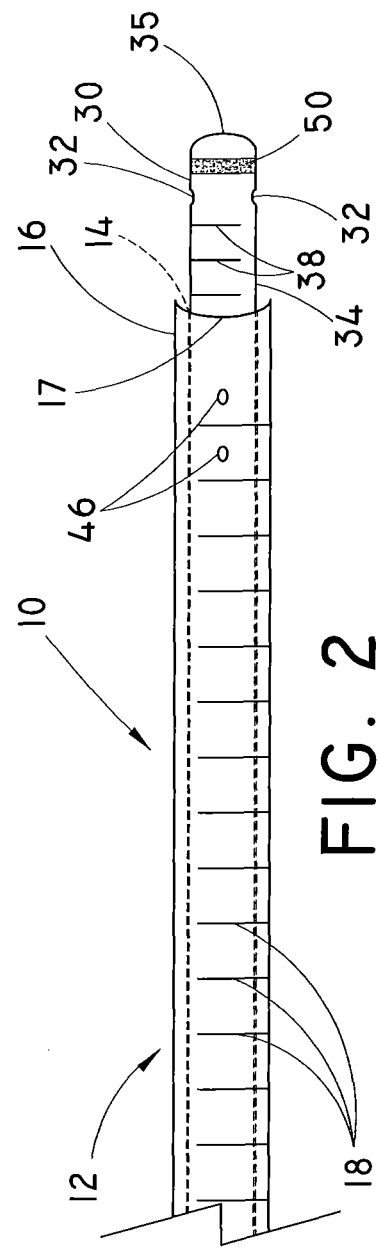

SYSTEM AND METHOD FOR FEEDING TUBE PLACEMENT

BACKGROUND OF THE INVENTION

1. Technical Field

The present invention relates to a system and method for positioning a device at a desired target location within a body canal of a patient. More particularly, the invention relates to a system and method for confirming proper placement of an end of feeding tube in the jejunum of a patient.

2. Background Information

Patients for whom normal ingestion of food becomes difficult or impossible may require placement of a feeding tube to assist in providing their nutritional needs. For some individuals, such as comatose patients, stroke victims, or those with a compromised gastrointestinal tract, this may require placement of a tube that is introduced percutaneously into the stomach for delivery of nutritional products directly into the stomach. Such tubes for delivery of nutritional products into the stomach are generally referred to as gastrostomy tubes, or "G"-tubes.

In some situations, feeding a patient through a G-tube can be problematic. Such situations include, among others, the presence of certain congenital abnormalities in the patient, as well as the possibility of severe gastric reflux and a high aspiration risk. In other situations, nutritional targets may not be attained at a satisfactory rate through G-tube feeding. In such patients, feeding may often be accomplished by inserting a feeding tube, sometimes referred to as a jejunostomy tube, or a "J"-tube, directly into the jejunum (the middle section of the small intestines) of the patient. The J-tube bypasses the stomach, thereby decreasing the risk of gastric reflux and aspiration. In addition, the J-tube often provides better success in reaching nutritional targets than a G-tube, and allows the targets to be reached more rapidly.

Notwithstanding the foregoing, however, there are some difficulties associated with the use of jejunostomy tubes. For example, due to the generally offset position of the jejunum relative to the stomach, it is often difficult to properly direct the distal end of a J-tube into the jejunum. J-tubes are typically very flexible, which contributes to the difficulty in directing the tubes to the desired area. In addition, once positioned, J-tubes are subject to dislodgement.

In view of the difficulties encountered in placing such tubes in the jejunum, radiographic imaging techniques, e.g., x-ray, are often utilized to verify proper placement of such tubes prior to transmission of food products therethrough. As health care workers must transport the patient to the radiology facility to obtain the x-ray, this technique increases the cost and complexity of the feeding tube placement. In addition, the use of x-ray exposes the patient to radiation. If the x-ray indicates that insufficient placement was achieved, then the verification process must be repeated following another attempt at placement. This adds still more cost and complexity to the procedure, and further increases the amount of radiation to which the patient is exposed.

It would be desirable to provide a system and method for placement of a feeding tube in the jejunum of the patient, in which proper placement of the feeding tube may be verified by less complex and intrusive means when compared to techniques previously carried out in the art.

BRIEF SUMMARY

The problems occurring in the art with regard to feeding tube placement verification are addressed with the system and method of the present invention. In one form thereof, a method is provided for monitoring a placement of an end of a feeding tube in the jejunum of a patient. An assembly comprises a feeding tube having a proximal portion, a distal portion, a passageway extending therethrough, and an open distal end. A tubular member having a proximal portion, a distal portion, and a closed distal end is received in the feeding tube passageway. The tubular member is sized such that a length of the distal portion extends distal to the feeding tube open end. The distal portion length has an opening formed therethrough, and includes an echogenic portion. The assembly is positioned for insertion through a body passage interiorly of the patient, and is advanced through the passage such that the feeding tube distal portion extends into the small intestine of the patient. A negative pressure is drawn in an interior space of the tubular member through the opening to draw the tubular member distal length into juxtaposition with a wall of the small intestine. Placement of the assembly is viewed via ultrasound visualization of the echogenic portion.

In another form thereof, the present invention is directed to a system for use in providing nutrition to a patient. A feeding tube has a proximal portion, a distal portion, a passageway extending between the proximal and distal portions, and an open distal end. The feeding tube is dimensioned for passage of the distal portion into the small intestine of the patient. An elongated tubular member receivable in the feeding tube passageway has a proximal portion, a distal portion, and a closed distal end. The elongated tubular member is sized such that a length of the distal portion extends distal to the feeding tube open distal end when the elongated tubular member is received in the feeding tube passageway. The distal portion length has one or more openings formed therein, and has an echogenic portion. A device is engageable with the proximal portion of the elongated tubular member for creating a negative pressure interiorly of the tubular member sufficient for juxtaposing the one or more openings with tissue of the small intestine. An ultrasound device provides a real-time image of the echogenic portion when the one or more openings are juxtaposed with the tissue.

A system for providing nutrition to a patient comprises a feeding tube having a proximal portion, a distal portion, a passageway extending between the proximal and distal portions, and an open distal end. The feeding tube is dimensioned for passage of the distal portion into the jejunum of the patient, and has a series of graduated markings disposed along a length thereof. An elongated tubular member receivable in the feeding tube passageway has a proximal portion, a distal portion, and a closed distal end. The elongated tubular member is sized such that a length of the proximal portion and a length of the distal portion extend beyond the respective proximal and distal portions of the feeding tube when the elongated tubular member is received in the feeding tube passageway. The distal portion length comprises about 3-5 cm, and has one or more openings formed therein. The distal portion length further includes an echogenic portion comprising a generally annular ring incorporated into the distal portion length and having a plurality of deformations along an outer surface of the ring. The elongated tubular member has a series of graduated markings disposed along its length. A syringe is removably engaged with the proximal portion of the elongated tubular member for creating a negative pressure interiorly of the tubular member sufficient for juxtaposing the one or more openings with tissue of the jejunum. An ultrasound device provides a real-time image of the echogenic portion when the one or more openings are juxtaposed with the tissue.

BRIEF DESCRIPTION OF THE DRAWINGS

FIG. 1 is a side view of the proximal portion of an embodiment of a feeding tube system;

FIG. 2 is a side view of the distal portion of the feeding tube system of FIG. 1;

DESCRIPTION OF PREFERRED EMBODIMENTS

Figure 3:
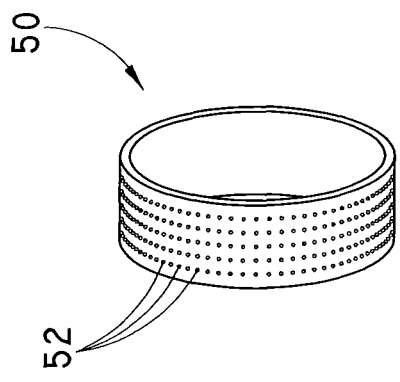
FIG. 3 is a side view of an annular ring having an echogenic surface.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates.

In the following discussion, the terms "proximal" and "distal" will be used to describe the opposing axial ends of the inventive system, as well as the opposing axial ends of various component features of the inventive system. The term "proximal" is used in its conventional sense to refer to the end of the system (or component thereof) that is closest to the operator during use. The term "distal" is used in its conventional sense to refer to the end of the system (or component thereof) that is initially inserted into the patient, or that is closest to the patient during use.

FIG. 1 is a side view of the proximal portion of a feeding tube system 10. FIG. 2 is a side view of the distal portion of the feeding tube system of FIG. 1. Feeding tube system 10 includes a feeding tube 12, and an elongated tubular member 30 removably received in an interior passageway 14 extending through feeding tube 12. Portions of elongated tubular member 30 extending through passageway 14 are shown in phantom. A suction device capable of creating a negative pressure within an interior space of elongated tubular member 30 is fitted at the proximal end of the tubular member. In this embodiment, the suction device is a syringe 40.

In a preferred embodiment, feeding tube 12 may comprise a naso-jejunal feeding tube, that is, a feeding tube that is inserted into the jejunum via the nasal cavity. However, those skilled in the art will appreciate that feeding tube 12 may be inserted into the jejunum other than through the nose, e.g., through the stomach or through the mouth. Alternatively, feeding tube 12 need not necessarily be used for delivering products into the jejunum, and delivery to other sites, such that alternative sites in the small bowel, may also be acceptable in some cases. Finally, although the fluid products delivered via the inventive system are generally referred to herein as food or nutritional products, it should be understood that other fluid materials, such as drugs and/or contrast materials, may also be delivered therethrough.

Feeding tube 12 comprises an elongated flexible tube having a proximal portion 15 and a distal portion 16. Preferably, feeding tube 12 includes a series of graduated markings 18 along its length to enable the technician to determine the depth of insertion of the feeding tube. As shown in FIG. 1, an optional adapter 20 is fitted at tubular member proximal portion 15. The adapter is sized to snugly fit over proximal portion 15 in any conventional manner. Adapter 20 is configured for engagement with a reservoir (not shown) for the fluid products in any well-known fashion, such as via a luer connection, for facilitating fluid communication between the reservoir and the interior passageway 14 of the feeding tube. In the embodiment shown, adapter 20 includes a generally hollow main body, a hinged lid 21, and a plug 22 on an interior surface of the hinged lid for selective closure of the interior passageway 14. Those skilled in the art will appreciate that mechanisms for connecting a feeding tube to a fluid reservoir are well known in the art, and that other suitable mechanisms may be substituted for the adapter shown herein.

As shown in FIG. 2, feeding tube 12 includes an open distal end 17 through which fluid products may pass into the jejunum. If desired, distal portion 16 may also include one or more feeding tube side ports, or apertures, 46 disposed along the distal portion of the tube for fluid flow. Feeding tube side ports are well known in the art, and when present, side ports 46 may have any dimensions commonly provided for such purposes.

Feeding tubes, such as naso-jejunal tubes, are well known in the art, and tube 12 may be formed from any compositions commonly used for such purposes. Polyurethane, PVC, and silicone are non-limiting examples of suitable compositions. Typically such tubes have a length of about 150-160 cm, and an outer diameter of between about 8 and 16 French (2.6 to 5.3 mm). Most commonly, the length of the tube is about 155 cm and the outer diameter is about 14 French (4.6 mm). The length and diameter of a feeding tube may be varied in well-known fashion to account for differences in patient size.

Those skilled in the art will appreciate that the feeding tube may include additional features well known in the art. For example, the outer surface of the feeding tube may be provided with a series of projections, such as cilia-like flaps, along the distal portion thereof. When present, such flaps or other projections advance the feeding tube into the small bowel via peristalsis. Feeding tubes having features that promote self-advancement by peristalsis are discussed in, for example, in U.S. Pat. Nos. 6,589,213 and 6,767,339, both incorporated by reference herein.

Elongated tubular member 30 comprises a closed-end tube that is received in the interior passageway 14 of feeding tube 12. Tubular member 30 may be formed of a composition similar to that of the feeding tube, such as polyurethane, PVC, or silicone. Preferably, however, tubular member 30 will have a durometer somewhat higher than that of the feeding tube. Thus, for example, if the feeding tube 12 and the elongated tubular member 30 are each formed of polyurethane, the tubular member 30 will be formed of a higher durometer polyurethane than that of the feeding tube. Providing a higher durometer material for the elongated tubular member minimizes a possibility that the tubular member will collapse inwardly when exposed to suction, as described hereinafter.

Elongated tubular member 30 has a proximal portion 31 and a distal portion 34. Elongated tubular member 30 may also have a series of graduated markings 38 along its length. Tubular member 30 will typically have a length such that both the proximal and distal portions 31, 34 extend beyond the respective proximal and distal ends of the feeding tube 12 by, e.g., about 3-5 cm each. Thus, for example, when the feeding tube has a length of about 150-160 cm as stated above, the elongated tubular member can have a length of about 160-170 cm. Preferably, tubular member 30 has an outer diameter only slightly less than the diameter of interior passageway 14 of the feeding tube 12. However, the tubular member outer diameter should permit free movement of the tubular member 30 through the interior passageway of the feeding tube. As discussed herein, tubular member 30 is removed from the interior passageway following verification of proper placement of the distal end of the feeding tube. Therefore, at least relatively free movement of the tubular member through the interior passageway is desirable to facilitate such withdrawal.

As shown in FIG. 2, the distal portion 34 of elongated tubular member 30 terminates in a closed distal tip 35. The length (3-5 cm in the example above) of distal portion 34 that extends beyond the distal end of feeding tube 12 includes one or more skived openings 32 formed along the circumference of the tubular member proximal to closed distal tip 35. In the embodiment shown, the openings comprise a pair of notches at opposing sides of the tubular member. Although the embodiment shown includes two notches, more, or fewer notches may be provided along the length of distal portion 34 distal of the feeding tube. Similarly, although the openings have been described as notches, openings of other configurations may be substituted. Openings 32 are dimensioned to draw tissue from the interior of the small bowel into juxtaposition with the adjoining portions of tubular member distal portion 34 upon exposure to suction forces, in a manner to be described. Openings 32 having a major diameter of about 0.5-1.0 cm are preferred, although other dimensions may be substituted.

Tubular member distal portion 34 includes an echogenic portion suitable for visualization under ultrasound. Echogenic enhancements for substrates are well known, and those skilled in the art will appreciate that many known enhancement mechanisms are suitable for use herein.

Figure 4:
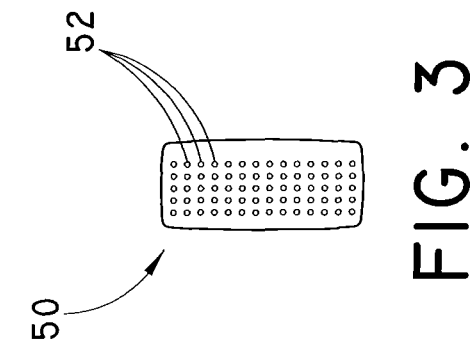
FIG. 4 is a perspective view of the annular ring of FIG. 3.

In one embodiment, an echogenically enhanced annular ring 50 is incorporated into distal portion 34 of the tubular member. One example of a suitable annular ring prior to incorporation into the tubular member is shown in FIGS. 3 and 4. Ring 50 may comprise, e.g., a ribbon wire that has been formed into the shape of an annular ring. Ribbon wire is well known for use in medical applications, and many such compositions may be utilized herein. Stainless steel and nitinol are non-limiting examples of suitable ribbon wire compositions. Ring 50 may have a diameter approximating that of tubular member 30, and a width of e.g., about 2-5 mm. When formed into the shape of the annular ring, echogenicity may be provided to the ring by providing a series of imperfections, such as deformations 52, along the outer surface of the ring. Deformations 52 may be formed along the ribbon wire by well-known processes, such as sandblasting, physical deformation, micro hammering, dimpling, etc.

The presence of deformations 52 along the surface of the ring causes ultrasound waves that contact the deformations to project therefrom in multiple directions and in random fashion. The increase in scatter and/or reflection of the ultrasound waves caused by the deformations enhances the temporal visualization of the tip of the feeding tube during ultrasound examination. By viewing the ultrasound signals created thereby, the health care worker may determine the location of the distal tip 34 of the tubular member 30 in real time.

Those skilled in the art will appreciate that ring 50 need not be formed from ribbon wire, and that other structures may be substituted. As one non-limiting example, ring 50 may comprise a suitably-dimensioned segment of a tubular member having deformations 52 along its outer surface. As another example, ring 50 may comprise a polymeric composition having an echogenic material, e.g., glass spheres, incorporated into the polymer.

Ring 50 may be incorporated into tubular member distal portion 34 in any suitable fashion. For example, the ring may be placed inside the distal portion 34 prior to closing the distal tip 31. Polymeric tubes such as tubular member 30 are typically closed by positioning the distal end in a suitably-shaped closure device, wherein the end is heated and formed to the desired configuration while in the heated state. In this case, annular ring 50 may be inserted into the interior passageway of the tubular member prior to tip closure. As the distal end is heated in the closure device, the heat to which the distal portion 34 is exposed softens the polymer such that ring 50 becomes trapped and sealed in the tubular member. In this case, the ring may be positioned as shown (in phantom) in FIG. 2. As another alternative, ring 50 may be positioned over the outer surface of tubular member distal portion 34. In this case, ring 50 can incorporated into the tubular member by well-known techniques, e.g., by melting of the tubular member distal portion, as described above, or by adhering the ring to the outer surface of the tubular member with a suitable adhesive.

Figure 5:
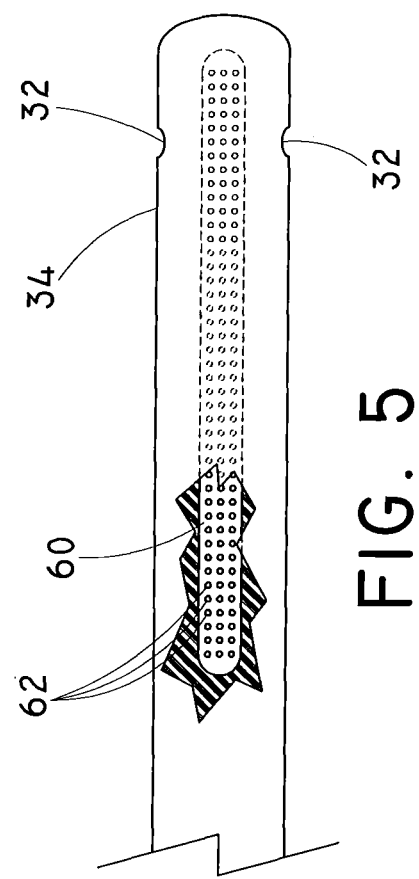
FIG. 5 illustrates an echogenic strip incorporated along a length of the tubular member of the feeding tube system.

Another way to incorporate echogenicity into tubular member 30 is to incorporate an echogenic strip along a length of the tubular member. For example, as shown in FIG. 5, a length of ribbon wire 60 as described above having deformations 62 along an outer surface of the wire may be incorporated into the tubular member. Similarly, an echogenic polymeric strip may be incorporated into the tubular member. One way to incorporate a length of ribbon in this manner is to position the wire along an extrusion line (deformations aligned so that they face outwardly in the finished tube), and to extrude the polymeric tubular member over the flattened length of wire. The distal portion 34 having the echogenic strip 60 incorporated therein is then closed as before.

Yet another means of incorporating echogenicity into the tubular member is to incorporate an echogenic material into the extrusion process for the tubular member. A non-limiting example of an echogenic material that may be incorporated in this manner is glass spheres. Glass spheres are frequently used to enhance echogenicity, and in this case, the spheres may be readily incorporated into the polymer during the extrusion process. Once this extrusion is formed, there would be no further need to add other materials to enhance echogenicity, as sufficient echogenicity for visualization under ultrasound is provided by the spheres.

Those skilled in the art will appreciate that there are many other ways in which enhanced echogenicity may be provided to a substrate, and that techniques other than those described herein may be utilized in providing echogenicity to the tubular member. For example, rather than providing a discrete echogenic ring or strip as described, a plurality of echogenic segments of a particular size and/or shape may be incorporated into the distal tip. If desired, echogenic segments can be spaced or otherwise positioned along the length of the distal tip in a manner such that the position of a discrete area of the tubular member distal end can be identified under ultrasound. However, for ease of manufacture and suitability of echogenic surface, the techniques described herein are presently preferred.

In the embodiment shown, a syringe 40 is removably engaged at the proximal end of elongated tubular member 30. Engagement may be accomplished by any conventional means, such as via mating luer connectors. Syringe luer connector 27 is shown in FIG. 1. Although the suction device shown in FIG. 1 is a syringe 40, this is merely one example of a suitable suction device, and other devices capable of drawing a negative pressure in the interior of tubular member 30 may be substituted. A conventional medical vacuum pump is one non-limiting example of an alternative device. For use herein, the suction device should be capable of drawing a negative pressure sufficient to bring the tubular member distal end 34 and the adjoining tissue of the body passageway into juxtaposition, as described herein. Those skilled in the art are readily capable of making any minor design modifications to the embodiments shown herein in order to incorporate a suction pump or like device instead of a syringe.

Many tubular canals and passageways in the body of a patient, such as the small intestine, have an air space extending therethrough. Ultrasound signals generally do not transmit well through such air spaces. Thus, if a tubular device is advanced through or otherwise positioned within such a passageway, attempts to visualize the device in the passageway via ultrasound may be problematic, if possible at all, due to the difficulty in penetrating the air space layer by the ultrasound waves. However, if the tissue lining the passageway is brought in contact with the device to be observed, or a discrete portion of the device, the ultrasound signals can travel through the tissue to the device.

In the system and method described herein, the tissue is brought in contact with the distal end of the tubular member by applying negative pressure, e.g., suction, through the elongated tubular member 30. This negative pressure acts through the notches 32, thereby bringing the tubular member distal end 34 and the adjoining tissue into juxtaposition with each other. Once contact is made, ultrasound visualization of the distal end can be carried out.

Figure 6:
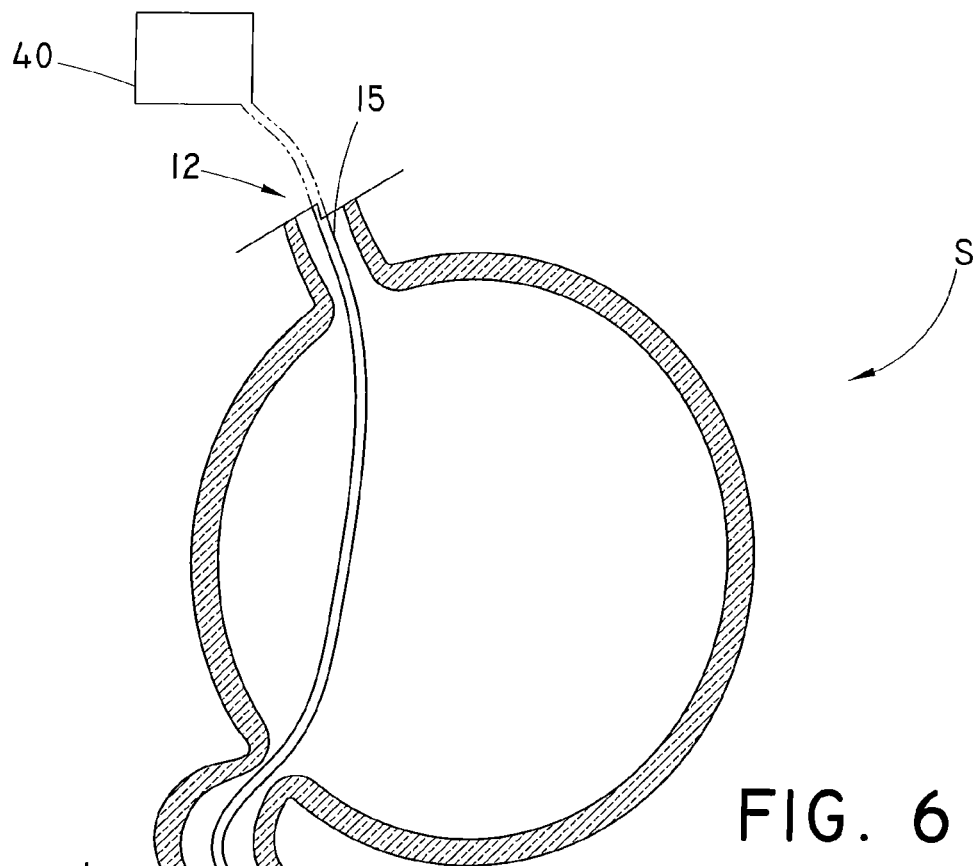
FIG. 6 illustrates the use of feeding tube system for confirming placement of the feeding tube in the jejunum of a patient.

FIG. 6 illustrates an example of the use of the system described herein for positioning a feeding tube 12, and for confirming proper placement of the distal end of the feeding tube in the small intestine. In this example, the distal end of a naso-jejunal feeding tube is inserted through the patient's nasal cavity, and is advanced into the stomach S. A conventional torque cable can be used if desired to assist in advancing the tube into the stomach. If the cable is used, it is removed once advancement into the stomach is achieved. Insufflation and auscultation may be used to confirm that the distal tip of the feeding tube is in the stomach. Following successful entry into the stomach, the feeding tube is further advanced in known fashion, e.g., via peristalsis, into the small intestine. Preferably, the feeding tube is advanced into the jejunum J, that is, the middle portion of the small intestine.

Once the distal opening 17 of the feeding tube is believed to have reached the jejunum, the next step is to confirm placement of the tip in the jejunum. As stated above, in the conventional insertion process, placement is confirmed by x-ray. This conventional process necessitates transporting the patient to a radiology facility, and exposing the patient to radiation from the x-rays at the facility. If it is determined that placement is insufficient, the patient must be returned to his/her room, and the process is repeated. When utilizing the feeding tube system described herein, proper placement may be confirmed by utilizing ultrasound visualization at bedside, and with no need to expose the patient to radiation.

When utilizing feeding tube system 10, tubular member 30 may be positioned within feeding tube interior passageway 14 prior to insertion of the feeding tube 12 through the stomach and into the jejunum. With this arrangement, the feeding tube and tubular member are inserted in tandem. Alternatively, feeding tube 12 may initially be inserted as described above, and tubular member 30 may be inserted through feeding tube interior passageway 14 following placement of the feeding tube. As stated above, feeding tube 12 and tubular member 30 will preferably be aligned such that tubular member distal end 34 extends approximately 3-5 cm beyond the distal open end 17 of the feeding tube.

Following placement of the feeding tube system 10, the suction device, e.g., syringe 40 in FIG. 1, is connected to proximal end 31 of tubular member 30, and activated to draw a negative pressure through the tubular member. The suction device 40 is shown schematically in FIG. 6. When the suction device is a syringe, activation of the syringe merely entails withdrawing plunger 41 in well-known fashion. If desired, water can be provided in the barrel of the syringe in well-known fashion to indicate via bubbles passing through the syringe barrel the continued withdrawal of air from the body passageway. As plunger 41 is withdrawn, the negative pressure generated acts on the tissue in the small bowel passageway, thereby drawing the notches of the elongated tubular member into juxtaposition with the tissue. A cessation of bubbling indicates that the notches and tissue are in contact.

Once the distal portion of the tubular member and the surrounding tissue are juxtaposed in this manner, the ultrasound device 66 (shown schematically in FIGS. 6 and 6A) is activated, and the ultrasound head is positioned along the skin of the patient exterior of the jejunum to direct ultrasound waves in the direction of the echogenic surface (e.g., ring 50) in tubular member distal portion 34. The use of ultrasound technology in medical applications is very well known, and the skilled artisan can readily select suitable apparatus for carrying out this ultrasound visualization. When the ultrasound waves reach the juxtaposed echogenic surface, the waves are scattered such that the ultrasound image can be viewed on an ultrasound monitor (not shown) in real-time. This real-time image informs the technician of the position of the echogenic surface of the tubular member, and therefore, the position of the feeding tube opening 17.

Figure 6A:
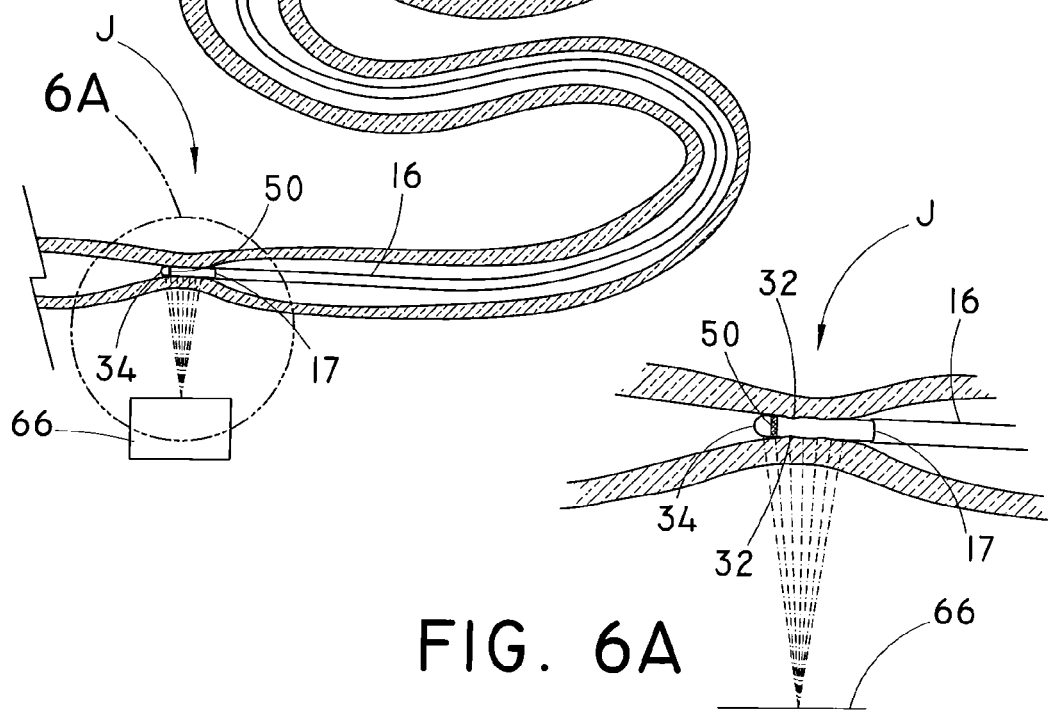
FIG. 6A is an enlarged view of a portion of FIG. 6.

If the ultrasound image confirms that the feeding tube tip is properly positioned in the jejunum, the suction may be terminated, whereupon the jejunal tissue retreats from its juxtaposed position with tubular member notches 32 shown in FIGS. 6 and 6A. Elongated tubular member 30 may then be withdrawn from the interior passageway 14 of the feeding tube. The feeding tube adapter is then engaged with the reservoir for the fluid products, and transmission of the fluid material into the jejunum can be carried out through the feeding tube in known fashion.

If it is determined that placement of feeding tube distal end 17 is unsatisfactory, then the placement of the feeding tube system 10 can be adjusted, the suction can be re-applied, and another ultrasound image may be obtained in the manner described above. This process can be repeated as many times as necessary until a suitable placement has been achieved.

Although not essential, it is preferred to provide both the feeding tube 12 and the elongated tubular member 30 with a series of graduated markings 18, 38 along all or a portion of their respective lengths. In this manner, a predetermined length of the feeding tube can be inserted into the patient, and an identical length of the elongated tubular member can also be inserted. At this time, the physician knows that the respective distal ends of the tubes are at the same depth. The elongated tubular member may then be advanced an additional distance, e.g., 3-5 cm. This enables the physician to ensure that the notched openings 32 are disposed distal to the feeding tube distal end 17. If desired, the respective proximal ends of the tubes can also be locked together, e.g., via a conventional locking clamp or the like, to hinder relative axial movement therebetween.

Although the system has been described herein in connection with one intended use, namely as a feeding tube system and a method for verifying a placement of the feeding tube, the system is not limited to this use. Rather, with minor modification, the system may also be used for verifying the placement of other types of tubes through body passageways.

While these features have been disclosed in connection with the illustrated preferred embodiments, other embodiments will be apparent to those skilled in the art that come within the spirit of the invention as defined in the following claims.

What is claimed is:

1. A method for monitoring a placement of an end of a feeding tube in the jejunum of a patient, comprising:
    positioning an assembly for insertion through a body passage interiorly of said patient, said assembly comprising a feeding tube having a proximal portion, a distal portion, a passageway extending therethrough, and an open distal end, and a tubular member received in said feeding tube passageway, the tubular member having a proximal portion, a distal portion, and a closed distal end, the tubular member sized such that a length of said distal portion extends distal to said feeding tube open end, said distal portion length having an opening formed therethrough and having an echogenic portion;
    advancing said assembly through said passage such that said feeding tube distal portion extends into the small intestine of the patient;
    drawing a negative pressure in an interior space of said tubular member through said opening to draw said tubular member distal length into juxtaposition with a wall of the small intestine; and
    viewing a placement of said assembly via ultrasound visualization of said echogenic portion.

2. The method of claim 1, wherein the assembly is advanced such that the feeding tube distal portion extends into the jejunum, and said ultrasound visualization confirms placement of said feeding tube distal portion in the jejunum.

3. The method of claim 2, further comprising removing said tubular member from said feeding tube passageway following confirmation of said placement.

4. The method of claim 2, wherein said length of said tubular member distal portion extends about 3-5 cm distal to said feeding tube open distal end.

5. The method of claim 1, further comprising:
    releasing said negative pressure;
    adjusting a position of said feeding tube distal portion in the small intestine;
    drawing a negative pressure in said interior space of said tubular member to once again draw said tubular member distal length into juxtaposition with said wall of the small intestine; and
    viewing a placement of said re-positioned assembly via ultrasound visualization of said echogenic portion.

6. The method of claim 1, wherein at least one of said feeding tube and elongated tubular member includes markings along a length thereof; wherein said negative pressure is drawn via a syringe; and wherein said echogenic portion comprises an annular ring positioned along said length of said tubular member distal portion, said annular ring having deformations formed along an outer surface thereof.

7. A system for use in providing nutrition to a patient, comprising:
    a feeding tube having a proximal portion, a distal portion, a passageway extending between said proximal and distal portions, and an open distal end, said feeding tube dimensioned for passage of said distal portion into the small intestine of the patient;
    an elongated tubular member receivable in said feeding tube passageway, said elongated tubular member having a proximal portion, a distal portion, and a closed distal end, said elongated tubular member sized such that a length of said distal portion extends distal to said feeding tube open distal end when said elongated tubular member is received in said feeding tube passageway, said distal portion length having one or more openings formed therein and having an echogenic portion;
    a device engageable with said proximal portion of said elongated tubular member for creating a negative pressure interiorly of said tubular member sufficient for juxtaposing said one or more openings with tissue of said small intestine; and
    an ultrasound device for providing a real-time image of said echogenic portion when said one or more openings are juxtaposed with said tissue.

8. The system of claim 7, wherein said length of said elongated tubular member extending distal to said feeding tube open end comprises about 3-5 cm.

9. The system of claim 7, wherein said elongated tubular member is dimensioned such that a length of said proximal portion extends proximal to said feeding tube proximal portion when said elongated tubular member is received in said feeding tube passageway.

10. The system of claim 7, wherein at least one of said feeding tube and elongated tubular member includes markings along a length thereof.

11. The system of claim 10, wherein each of said feeding tube and elongated tubular member includes markings along a length thereof.

12. The system of claim 7, wherein said openings formed in said distal portion length comprise at least two notches formed at opposing sides of said elongated tubular member.

13. The system of claim 7, wherein said echogenic portion comprises a generally annular ring disposed in said length of said tubular member distal portion.

14. The system of claim 13, wherein said generally annular ring has deformations on an outer surface thereof.

15. The system of claim 7, wherein said echogenic portion comprises an echogenic strip positioned along said distal portion length.

16. The system of claim 7, wherein said echogenic portion comprises an echogenic material incorporated into a matrix of said elongated tubular member.

17. The system of claim 7, wherein said device for creating a negative pressure comprises a syringe.

18. A system for providing nutrition to a patient, comprising:
    a feeding tube having a proximal portion, a distal portion, a passageway extending between said proximal and distal portions, and an open distal end, said feeding tube dimensioned for passage of said distal portion into the jejunum of the patient, said feeding tube having a series of graduated markings disposed along a length thereof;
    an elongated tubular member receivable in said feeding tube passageway, said elongated tubular member having a proximal portion, a distal portion, and a closed distal end, said elongated tubular member sized such that a length of said proximal portion and a length of said distal portion extend beyond the respective proximal and distal portions of said feeding tube when said elongated tubular member is received in said feeding tube passageway, said distal portion length comprising about 3-5 cm and having one or more openings formed therein, said distal portion length further comprising an echogenic portion, said echogenic portion comprising a generally annular ring incorporated into said distal portion length and having a plurality of deformations along an outer surface of the ring, said elongated tubular member having a series of graduated markings disposed along its length;

a syringe removably engaged with said proximal portion of said elongated tubular member for creating a negative pressure interiorly of said tubular member sufficient for juxtaposing said one or more openings with tissue of said jejunum; and an ultrasound device for providing a real-time image of said echogenic portion when said one or more openings are juxtaposed with said tissue.

\* \* \* \* \*